(12) United States Patent
Fitzmaurice

(10) Patent No.: US 10,448,809 B2
(45) Date of Patent: Oct. 22, 2019

(54) PROTECTIVE SHEATH FOR AN ENDOSCOPE

(71) Applicant: Michael James Fitzmaurice, Scottsdale, AZ (US)

(72) Inventor: Michael James Fitzmaurice, Scottsdale, AZ (US)

(*) Notice: Subject to any disclaimer, the term of this patent is extended or adjusted under 35 U.S.C. 154(b) by 0 days.

(21) Appl. No.: 13/912,312

(22) Filed: Jun. 7, 2013

(65) Prior Publication Data

US 2013/0345515 A1    Dec. 26, 2013

Related U.S. Application Data

(60) Provisional application No. 61/656,989, filed on Jun. 7, 2012.

(51) Int. Cl.
| | |
|---|---|
| *A61B 1/00* | (2006.01) |
| *A61B 1/04* | (2006.01) |
| *A61B 1/32* | (2006.01) |
| *A61B 1/317* | (2006.01) |
| *A61B 17/32* | (2006.01) |
| *A61B 17/00* | (2006.01) |

(52) U.S. Cl.
CPC ...... *A61B 1/00135* (2013.01); *A61B 1/00087* (2013.01); *A61B 1/04* (2013.01); *A61B 1/317* (2013.01); *A61B 1/32* (2013.01); *A61B 17/320036* (2013.01); *A61B 2017/00296* (2013.01)

(58) Field of Classification Search
CPC ......... A61B 1/00135; A61B 1/04; A61B 1/32; A61B 1/317; A61B 2017/00296; A61B 17/320036; A61B 1/00087

USPC .................................. 600/121, 122, 208
See application file for complete search history.

(56) References Cited

U.S. PATENT DOCUMENTS

| | | | | |
|---|---|---|---|---|
| 3,900,021 | A * | 8/1975 | Makepeace et al. ......... | 600/112 |
| 5,323,765 | A * | 6/1994 | Brown ........... | A61B 17/320036 |
| | | | | 128/898 |
| 5,681,262 | A * | 10/1997 | Isse ........................ | A61B 1/012 |
| | | | | 600/104 |
| 6,979,318 | B1 * | 12/2005 | McDonald et al. ......... | 604/158 |
| 2008/0200758 | A1 * | 8/2008 | Orbay et al. ............. | A61B 1/04 |
| | | | | 600/112 |
| 2008/0255600 | A1 * | 10/2008 | Braam ............. | A61B 17/00008 |
| | | | | 606/190 |
| 2011/0112376 | A1 * | 5/2011 | Vayser et al. ................ | 600/249 |

FOREIGN PATENT DOCUMENTS

EP    0552980    9/1997

* cited by examiner

*Primary Examiner* — Timothy J Neal
(74) *Attorney, Agent, or Firm* — Richard E. Oney; Venjuris, P.C.

(57) ABSTRACT

A protective sheath for an endoscope includes an elongated shaft with a longitudinal bore extending from a proximal opening at the shaft proximal end to a distal opening at the shaft distal end. The longitudinal bore is sized for receiving an endoscope tube inserted axially into the bore. The shaft distal end includes a shovel-shaped portion comprising a bowl, a bowl rim having a flange portion, and a distal cutting edge for dividing soft tissue a surgical procedure. The surfaces of the shovel-shaped portion are adapted for retracting soft tissue during such a procedure.

20 Claims, 12 Drawing Sheets

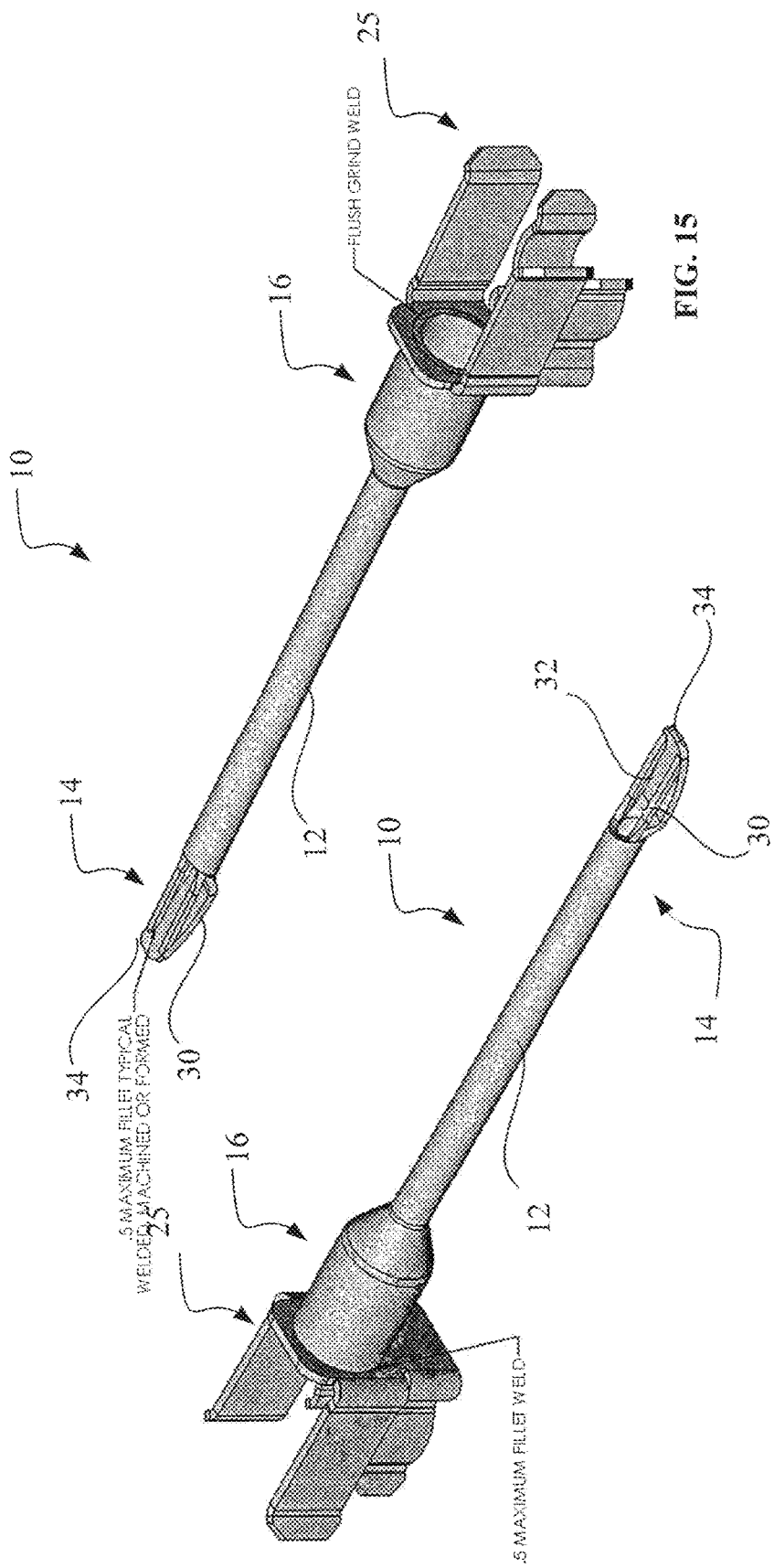

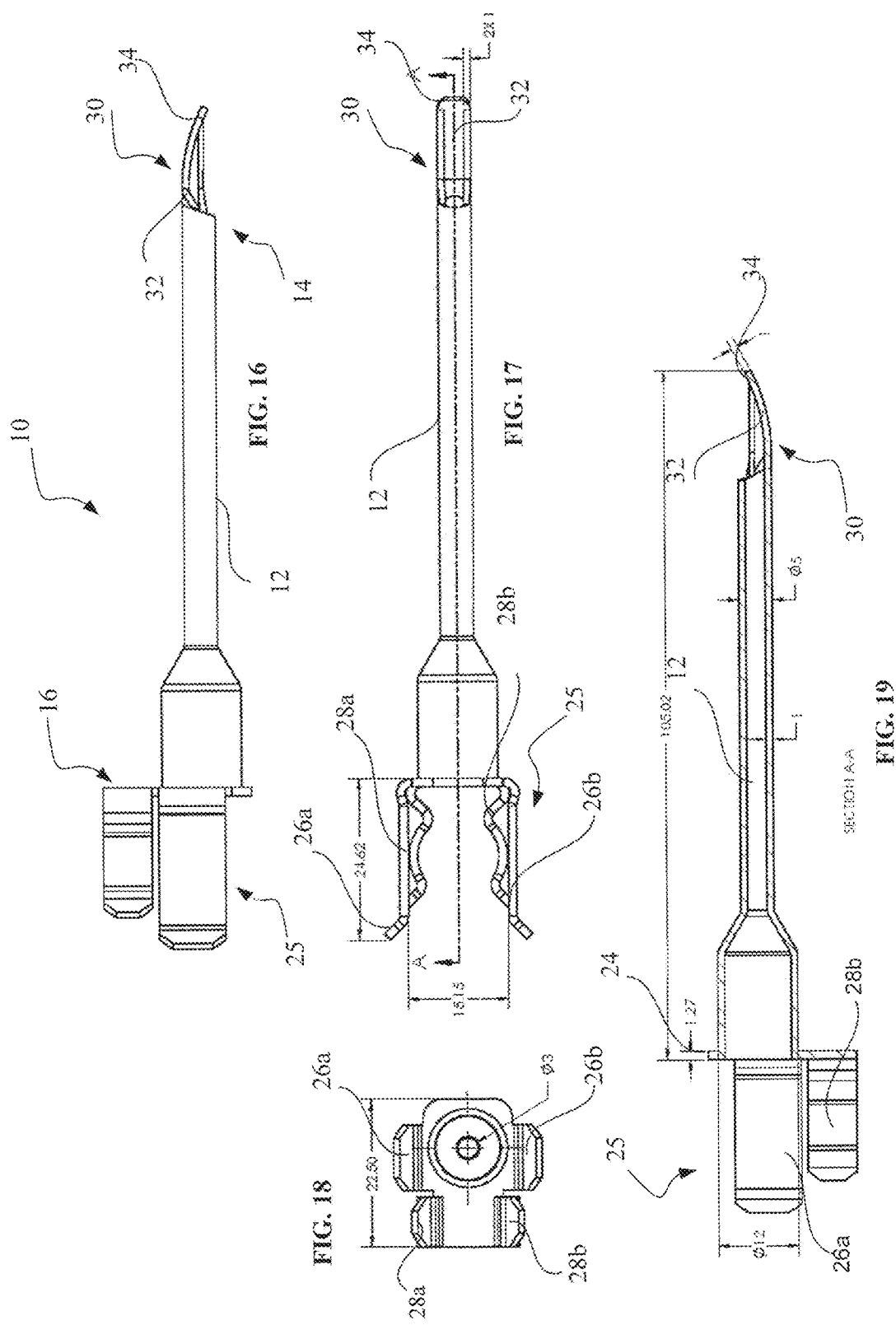

PROTECTIVE SHEATH FOR AN ENDOSCOPE

RELATED APPLICATION

This application claims the benefit of U.S. Provisional Application No. 61/656,989, filed Jun. 7, 2012, entitled "Protective Sheath for an Endoscope," which is incorporated herein by reference.

BACKGROUND

This invention relates to apparatus for use in performing endoscopic surgical procedures. More particularly, the invention relates to an improved sheath for an endoscope for performing surgical procedures requiring fibrous tissue division, such as an endoscopic procedure for carpal tunnel release.

Because of the trauma associated with open surgical procedures, efforts have been made to develop endoscopic alternatives to all types of open surgical procedures. This invention relates to endoscopic alternatives to open procedure for surgical treatments requiring division of soft tissue, such as a tendon sheath or ligament. One example of such a procedure is the treatment of carpal tunnel syndrome, caused by the compression of the median nerve by the transverse carpal ligament. This treatment generally involves a procedure during which the carpal ligament is severed. While endoscopic versions of this procedure have been used in the past with varying degrees of success, continued development of endoscopic procedures to improve efficiencies and reduce patient trauma is always desirable.

For example, the prior endoscopic treatments of carpel tunnel syndrome described by Chow in U.S. Pat. No. 5,029,573 and by Brown in U.S. Pat. No. 5,323,765 use a slotted cannula design that is positioned under the transverse carpal ligament during the procedure. This places pressure on the nerve during the procedures and also places the nerve and tendons at risk of injury. Moreover, a number of prior endoscopic procedures for carpel tunnel release require two incisions (with one being in the palm) and/or require the introduction of one or more obturators into the carpel tunnel before insertion of the endoscope, which can cause additional trauma to the surgery site.

Accordingly, it is an object of the present invention to produce an endoscopic surgical apparatus suitable for use in various surgical procedures that involve the dissection and/or other retraction of fibrous tissue, including an endoscopic procedure for carpal ligament release as well as other endoscopic surgical procedures.

It is another object of the invention to provide an apparatus for performing such endoscopic surgical procedures with less trauma than existing endoscopic procedures.

It is another object of the present invention to provide an apparatus that facilitates the alignment of a cannula over the carpal ligament.

Although one preferred embodiment of this invention relates to carpal ligament release, it will be understood by those skilled in the art that the apparatus disclosed herein may be easily adapted to other surgical procedures.

Additional objects and advantages of the invention will be set forth in the description that follows, and in part will be apparent from the description, or may be learned by practice of the invention. The objects and advantages of the invention may be realized and obtained by means of the instrumentalities and combinations pointed out in the appended claims.

SUMMARY

To achieve the foregoing objects, and in accordance with the purposes of the invention as embodied and broadly described in this document, there is provided a protective sheath for an endoscope that includes an elongated shaft with a distal end and a proximal end. The shaft has a longitudinal bore extending from a proximal opening at the shaft proximal end to a distal opening at the shaft distal end. The longitudinal bore is sized for receiving an endoscope tube inserted axially into the bore from the proximal end. The shaft distal end includes a shovel-shaped portion comprising a bowl, a bowl rim having a flange portion, and a distal cutting edge for cutting soft tissue. The sheath proximal end includes a clip configured for attachment to an endoscopic camera.

According to one advantageous aspect of the invention, one or more surfaces of the shovel-shaped portion are adapted for retracting soft tissue during a surgical procedure. In one embodiment, the bowl comprises a sidewall extending upward from a floor. The sidewall can include a light-reflective surface.

According to one advantageous aspect of the invention, the configuration of the allows for its placement above a transverse carpel ligament (rather than below the ligament) during a carpel ligament release procedure.

BRIEF DESCRIPTION OF THE DRAWINGS

The accompanying drawings, which are incorporated in and constitute a part of the specification, illustrate the presently preferred embodiments and methods of the invention and, together with the general description given above and the detailed description of the preferred embodiments and methods given below, serve to explain the principles of the invention.

FIG. 14 is a top perspective view of an alternative embodiment of a sheath according to the present invention.

FIG. 15 is another top perspective view of the sheath of FIG. 14.

FIG. 16 is a side elevation view of the sheath shown in FIG. 14.

FIG. 17 is top plan view of the sheath shown in FIG. 14.

FIG. 18 is an elevation view of the proximal end of the sheath shown in FIG. 14.

FIG. 19 is a cross-sectional view taken along the line A-A shown in FIG. 17.

DESCRIPTION

Figure 1:
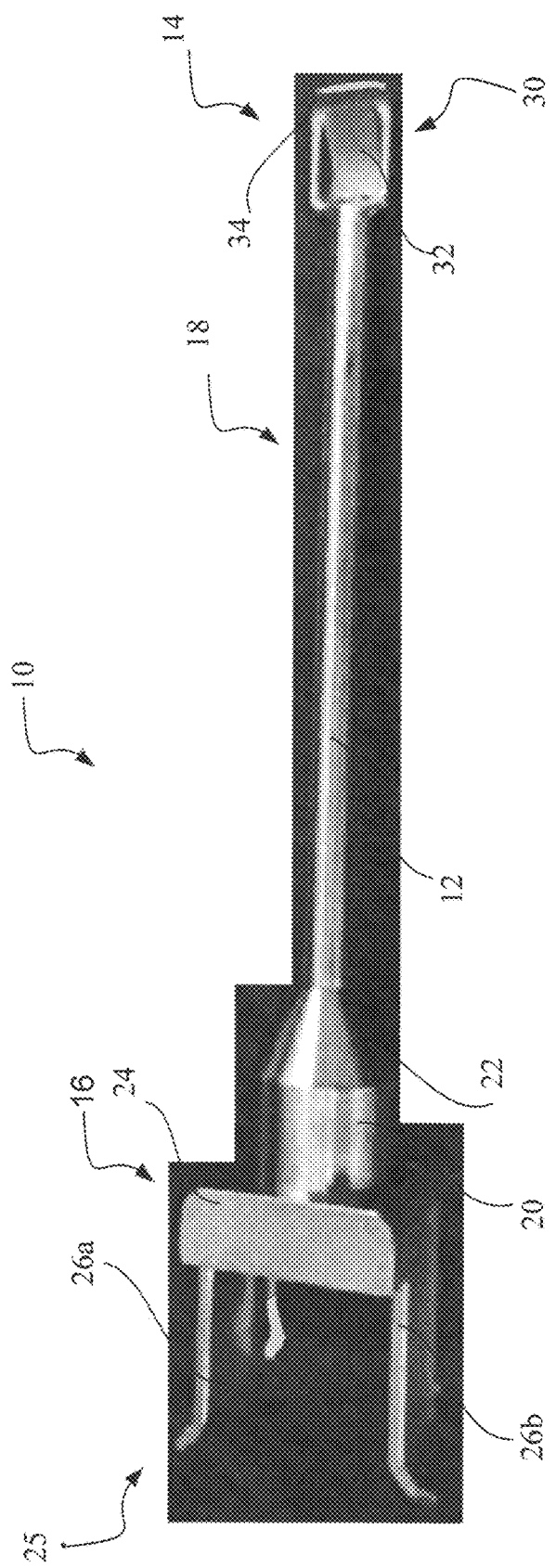
FIG. 1 is a top perspective view of one embodiment of a sheath according to the present invention.

Reference will now be made in more detail to presently preferred embodiments of the invention, as illustrated in the accompanying drawings. While the invention is described more fully with reference to these examples and drawings, the invention in its broader aspects is not limited to the specific details, representative devices, and illustrative examples shown and described. Rather, the description which follows is to be understood as a broad, teaching disclosure directed to persons of ordinary skill in the appropriate arts, and not as limiting upon the invention.

As used herein, the term "endoscope" is intended to be generic and refers to any type of optical system used to view the interior of a patient. It also will be appreciated that terms such as "upper," "inner," "outer," "vertical," "horizontal," "bottom," "below," "top," "side," "inwardly," "outwardly," "downwardly" and "lower" and other positionally descriptive terms used in this specification are used merely for ease of description and refer to the orientation of the referenced components as shown in the figures. It should be understood that any orientation of the components described herein is within the scope of the present invention. The term "generally" as used in this specification is defined as "being in general but not necessarily exactly or wholly that which is specified." For example, "generally perpendicular" is used herein to indicate components that are in general, but not necessarily exactly or wholly, perpendicular.

In the drawings, the reference numeral 10 designates a protective sheath for an endoscope in accordance with the invention. The sheath 10 comprises an elongated cannula or tubular shaft 12 with a longitudinal bore 17 extending along the axis of the cannula 12 from an opening at a proximal end 16 to an opening at a distal end 14. The shaft 12 includes a distal shaft section 18 at to the distal end 14, a larger-diameter proximal shaft section 20 at to the proximal end 16, and a tapered shaft section 22 intermediate the distal shaft section 18 and the proximal shaft section 20.

The width of the bore 17 should be sufficient to enable the chosen endoscope to slide freely into the bore 17. If it is too wide, the surgeon would have to be too concerned about aiming the scope. In one presently preferred embodiment, the portion of the bore 17 within the distal shaft section 18 is from about 0.11 to 0.12 inches (or from about 2.7 to 3.0 millimeters). In this configuration, the bore 17 can accept a standard 2.7 millimeter endoscope tube. To permit easy insertion of an endoscope tube into the sheath 10, the bore 17 is enlarged inside the proximal shaft section 20 and is tapered in the tapered shaft section 22.

Figure 2:
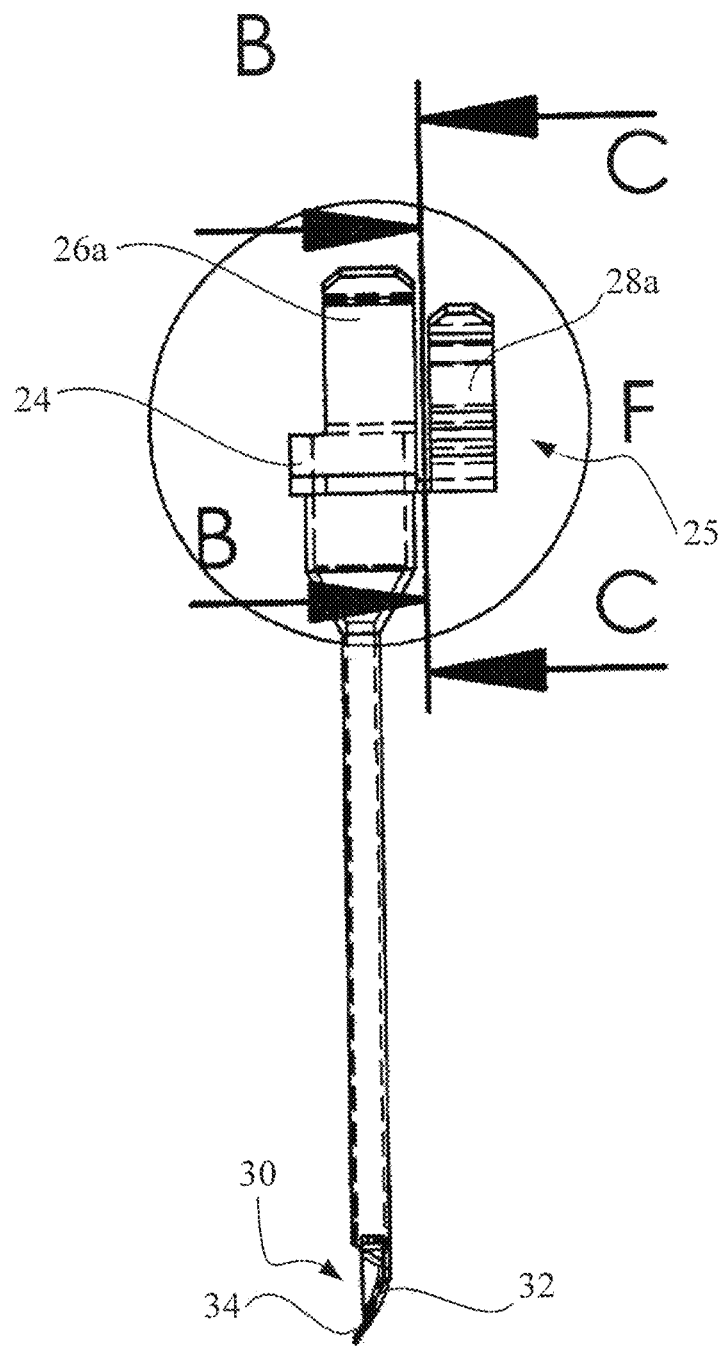
FIG. 2 is a side elevation view of the sheath shown in FIG. 1.
Figure 3:
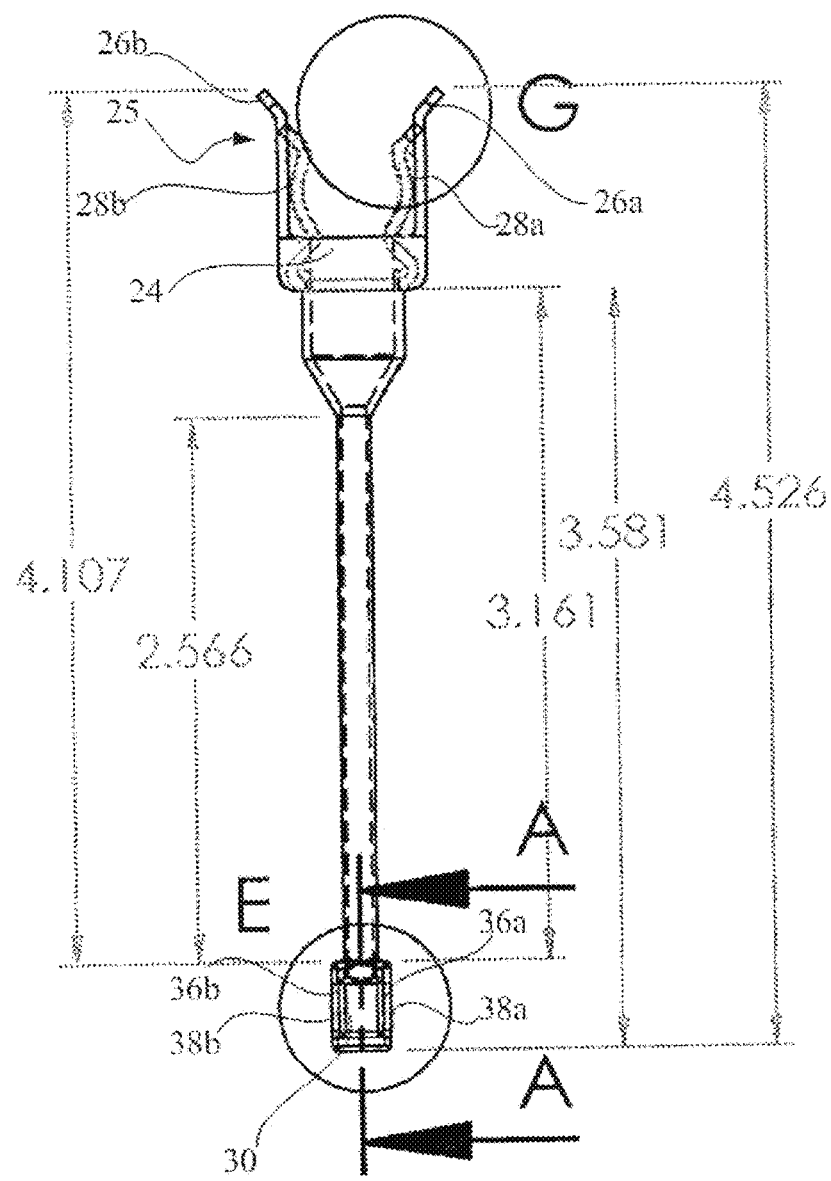
FIG. 3 is top plan view of the sheath shown in FIG. 1.
Figure 4:
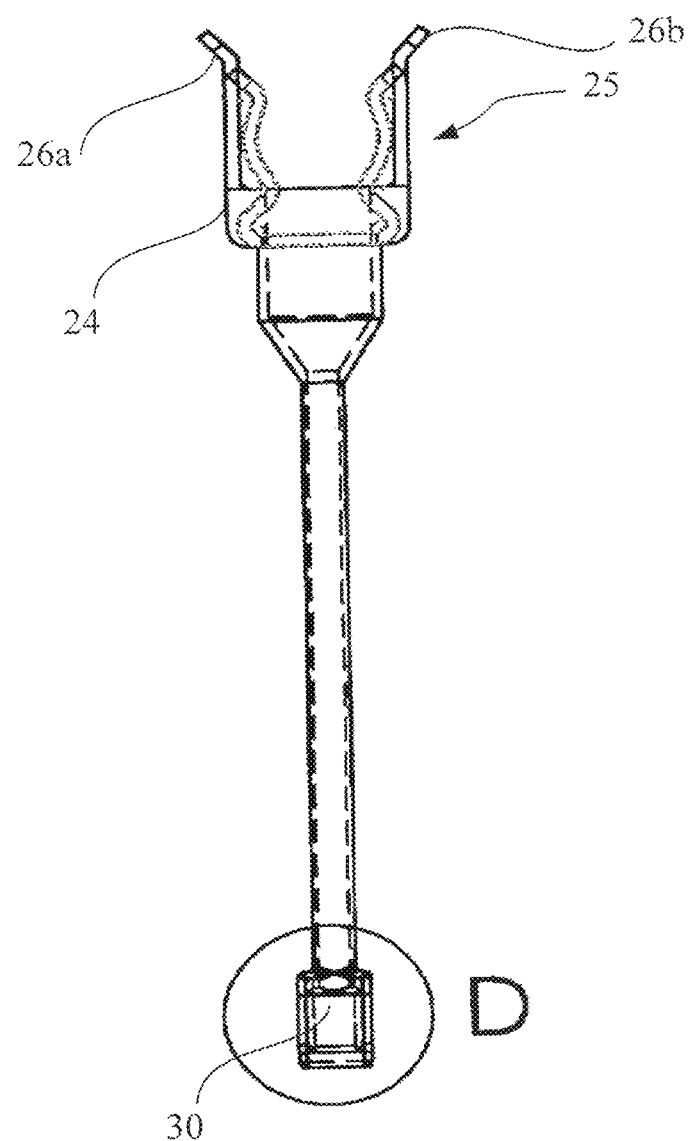
FIG. 4 is a bottom plan view of the sheath shown in FIG. 1.
Figure 6:
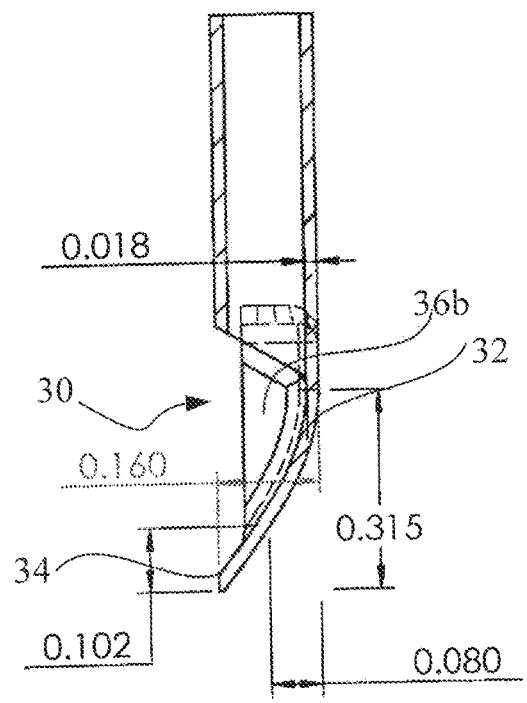
FIG. 6 is a cross-sectional view taken along the line A-A shown in FIG. 1.
Figure 9:
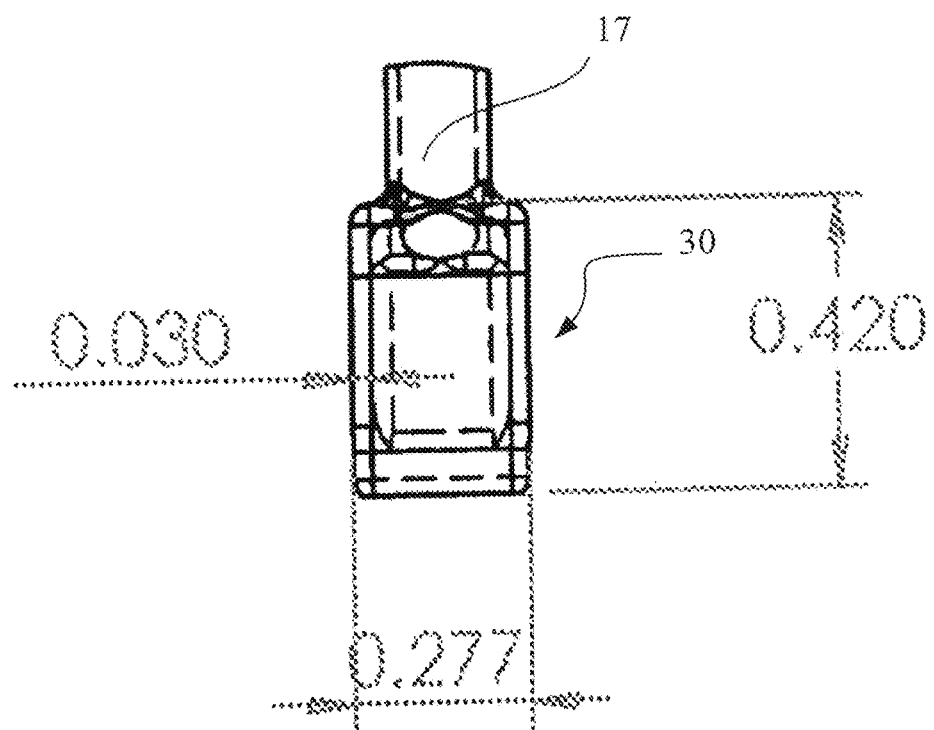
FIG. 9 is an enlarged view of a portion of the sheath of FIG. 1, which portion is referenced as detail D in FIG. 4.
Figure 10:
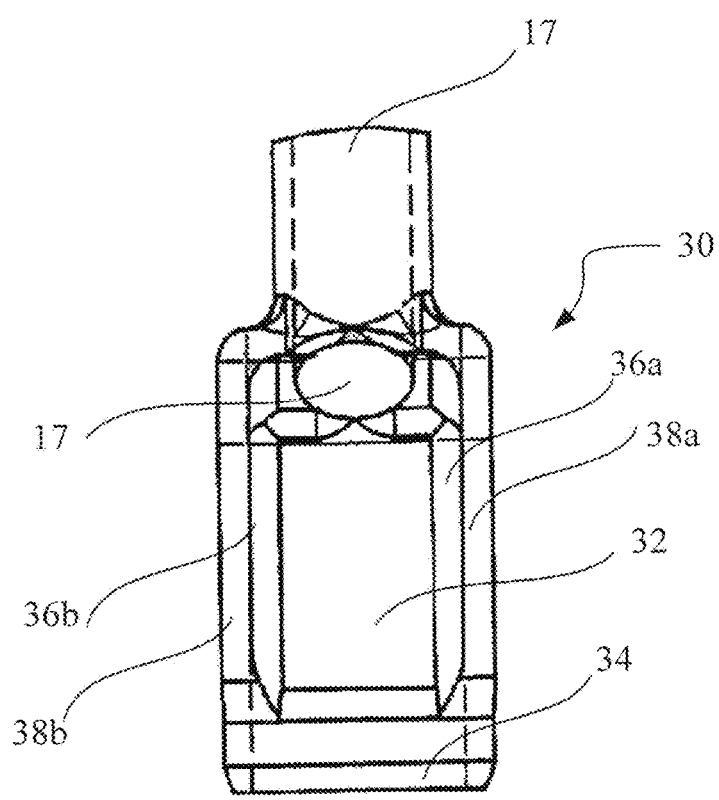
FIG. 10 is an enlarged view of a portion of the sheath of FIG. 1, which portion is referenced as detail E in FIG. 3.

The distal end 14 includes a generally shovel-shaped portion 30, which is used to assist with the dissection and retraction of soft tissue during use. As shown in FIGS. 2-4, 6 and 9-10, in one embodiment, the shovel 30 includes a floor 32 that curves gradually upward and terminates at its distal end in a relatively flat edge to form a cutting tip 34. Two angled sidewalls 36a, 36b extend upward from the shovel floor 30 and terminate in sidewall flanges 38a, 38b, to form side rims along the top of the shovel bowl 32. In this configuration, the cutting tip 34 can be used to dissect soft tissue during a procedure, and the outer surfaces of the sidewalls 36, the bowl floor 32 and the sidewall flanges 38 can be used to assist with the retraction of soft tissue (e.g., muscle and fat) during a procedure. In a presently preferred embodiment, the sidewalls are solid and are light-reflective to reflect light transmitted from the endoscope tube toward the desired work site. However in an alternative embodiment, as shown in FIGS. 14-19, the shovel side walls 36 can include orifices.

Figure 5:
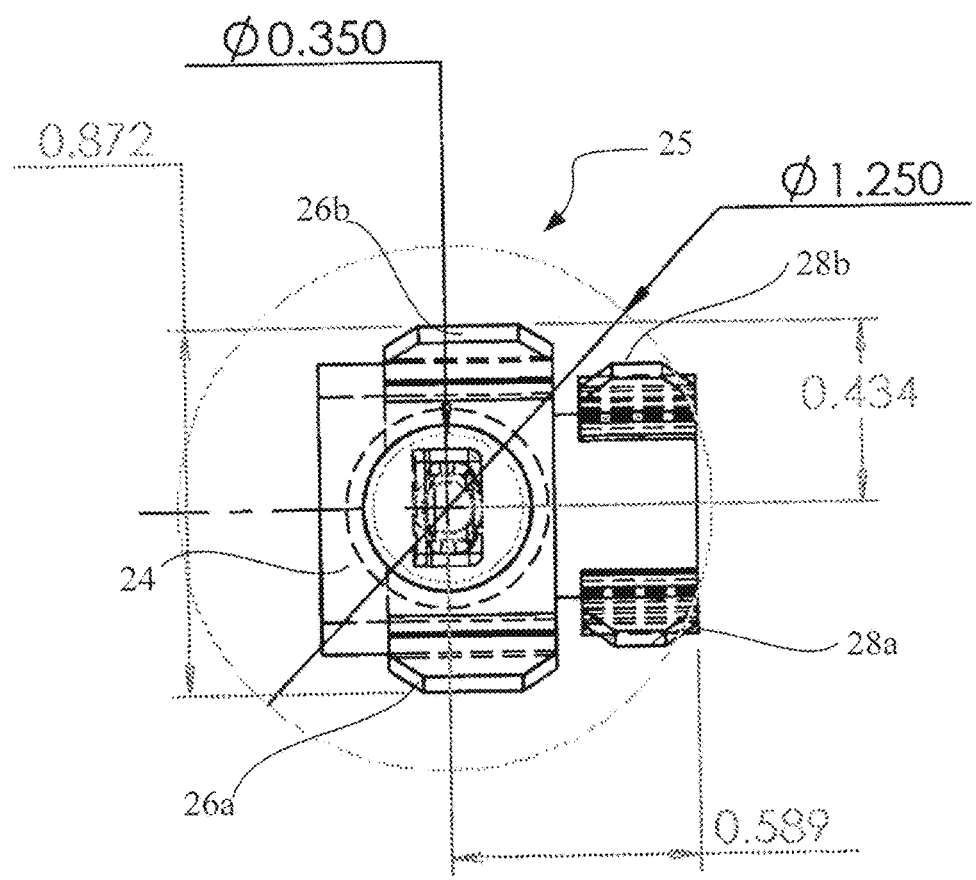
FIG. 5 is an elevation view of the proximal end of the sheath shown in FIG. 1.
Figure 7:
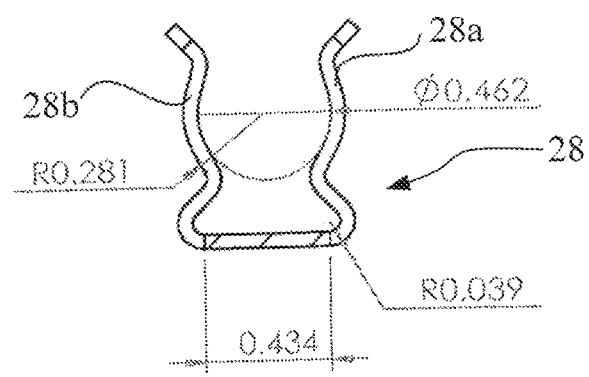
FIG. 7 is a cross-sectional view taken along the line B-B shown in FIG. 2.
Figure 8:
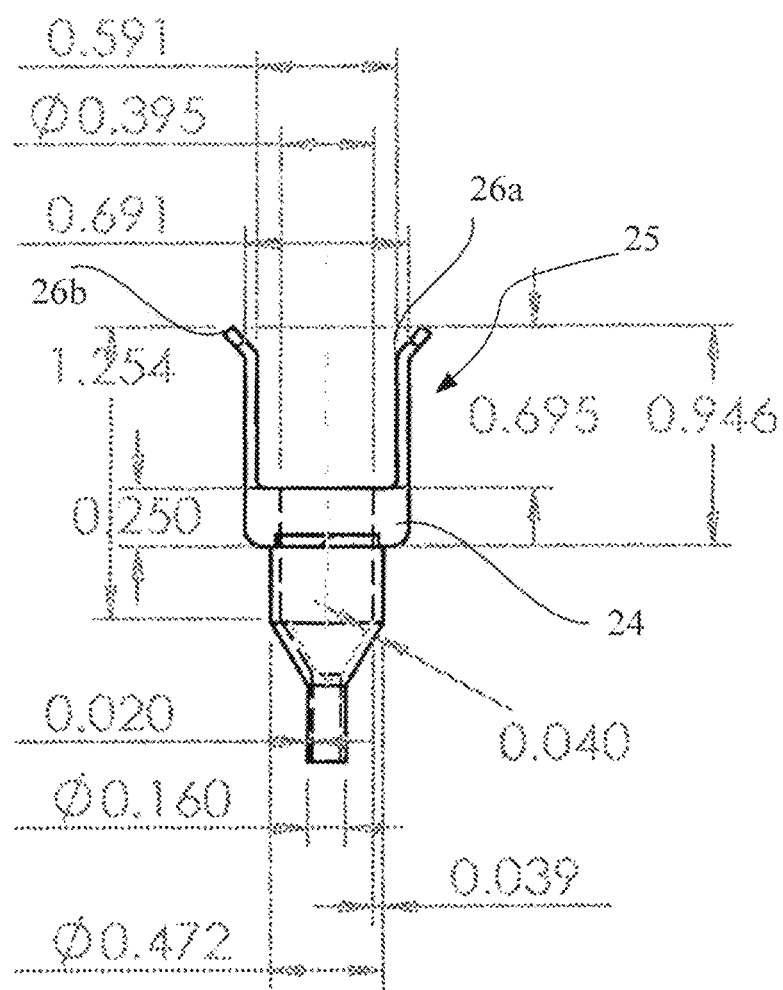
FIG. 8 is a cross-sectional view taken along the line C-C shown in FIG. 2.
Figure 11:
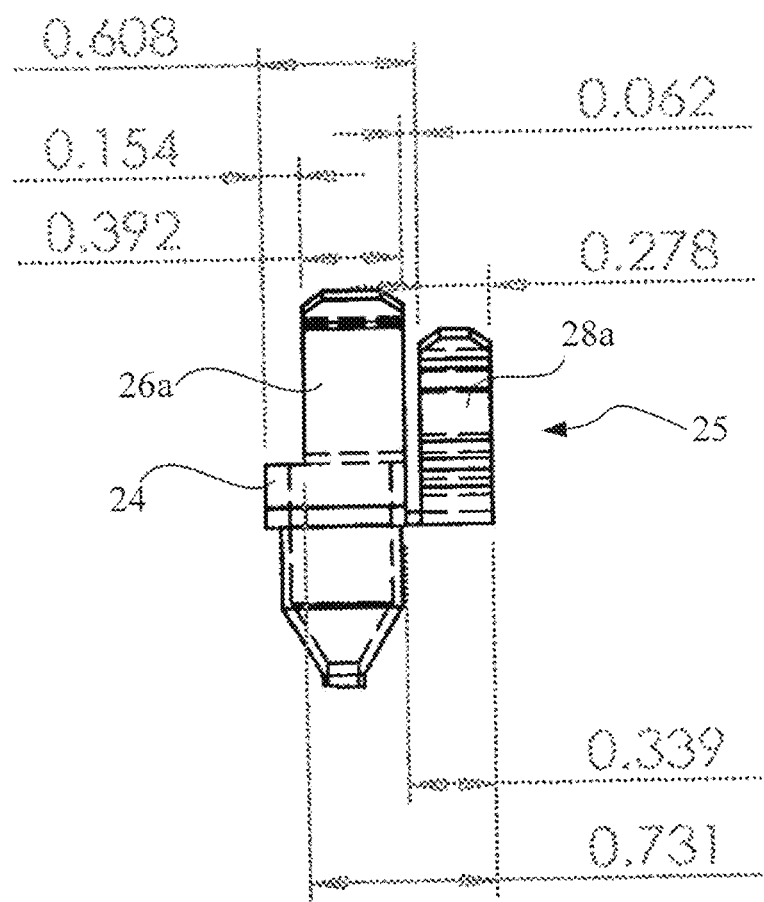
FIG. 11 is an enlarged view of a portion of the sheath of FIG. 1, which portion is referenced as detail F in FIG. 2.
Figure 12:
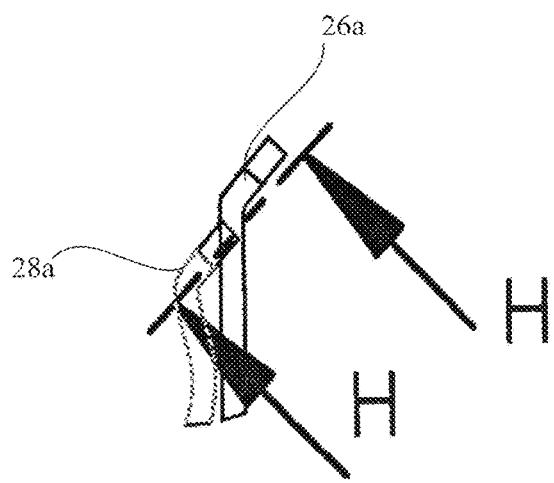
FIG. 12 is an enlarged view of a portion of the sheath of FIG. 1, which portion is referenced as detail G in FIG. 3.

The shaft proximal end 16 includes a collar 24 to which is attached an attachment mechanism 25 for secure attachment to the face of an endoscopic camera to prevent rotation or longitudinal movement of the camera and the endoscopic tube with respect to the sheath 10. As shown in FIGS. 2-5, 7-8 and 11, in a presently preferred embodiment, the collar 24 is in the shape of generally rectangular plate and the attachment mechanism 25 includes an upper clip 26 (comprising a pair of upper clip prongs 26a,26b) and a lower clip 28 (comprising a pair of lower clip prongs 28a, 28b). In this configuration, the collar 24 and attachment mechanism are configured to easily and securely attach to the face of an endoscopic camera such as those marketed by Stryker Corporation of Kalamazoo, Mich.

Figure 13:
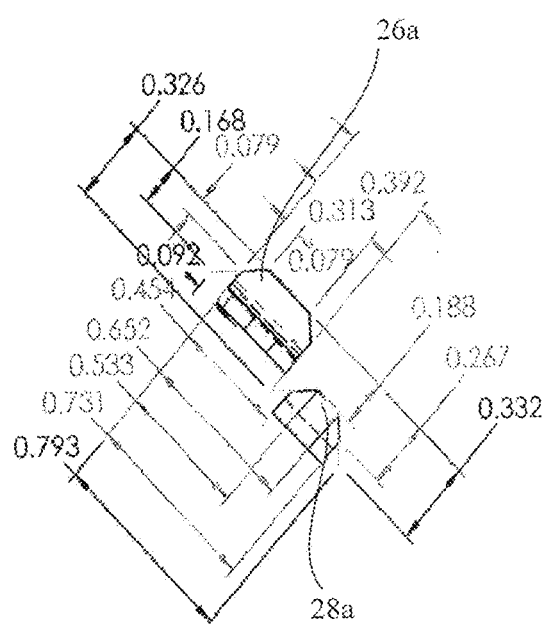
FIG. 13 is a cross-sectional view taken along the line H-H shown in FIG. 12.

While any known material can be used to build this device, it is preferable to use medical grade stainless steel. Similarly, it is preferred to build the entire protective sheath for an endoscope out of a single piece of piece of material, such as by machining the device from a single stainless steel work-piece. However, the device can be built with any known metalworking technique. Exemplary dimensions of one embodiment of the sheath 10 are shown (in inches) in FIGS. 3, 5-9, 11 and 13, and exemplary dimensions of an alternative embodiment are shown in (in millimeters) in FIGS. 17-19.

To use the device a physician simply slides the endoscope tube (not shown) into the bore 17 through the opening in the collar 24 and through the proximal shaft section 20, the tapered section 22 and the distal shaft section 18 so that the endoscope rests on the shovel bowl 32 at the distal end 14 of the device. The endoscope can then be used to illuminate and view the work area as is known in the art.

For performing endoscopic tendon surgery, the sheath 10 can be placed over an endoscope and inserted into the area of dissection. The sheath 10 then facilitates dissection of the soft tissues over the tendon with visualization and retraction of the nerves to allow release of the tight tunnel for the tendon. For nerve surgery, the sheath 10 also can be placed over an endoscope and inserted into the area of dissection. The sheath 10 facilitates retraction of soft tissues and visualization of the nerves. Because of the free movement allowed with the instrument, small scissors can then be placed to perform release of scar tissue or placement of anti-adhesive barriers to prevent further scar tissue.

The device can be used in a number of different endoscopic procedures, including the following:

Endoscopic carpal tunnel release
Endoscopic cubital tunnel release
Endoscopic pronator release
Endoscopic De Quervains release
Endoscopic trigger finger release
Endoscopic trigger thumb release
Endoscopic tennis elbow surgery
Endoscopic tenolysis for adhesions
Endoscopic tendon transfer
Endoscopic Dupuytren's fasciectomy For illustrative purposes, certain of these procedures will now be described in more detail.

Procedure for Endoscopic Dequervain's Release

The first dorsal compartment is palpated over the radial styloid and a 5-10 mm transverse incision is marked between the radial styloid and base of first metacarpal. The incision is carried down through the skin and subcutaneous tissue until the tendons of the first dorsal compartment (APL, EPB) are visualized. Next, the endoscopic sheath 10 is placed over an endoscopic camera and locked into position. The sheath and camera are then placed into the incision from a distal to proximal direction obtaining visualization of the first dorsal compartment tendons. The cutting tip 34 of the sheath 10 is then used to dissect over the first dorsal compartment from distal to proximal. If the superficial branch of the radial nerve is identified over the compartment, it can be retracted away from the field using the shovel 30 of the sheath 10. The thickened compartment is then divided along the middle portion of the compartment from distal to proximal direction using tenotomy scissors. This will leave approximately equal flaps on either side to prevent subluxation of the tendons. Next, the thumb is placed through a full passive flexion and extension motion to ensure complete release of the compartment. The sheath 10 is then used to visualize the compartment release and identify any separate compartments. Any separate compartments can then be released under direct visualization of the endoscopic sheath 10 and tenotomy scissors dividing the additional compartments in a distal to proximal direction. The sheath 10 and camera are then removed slowly while ensuring complete release of all compartments within the first dorsal compartment region. The skin edges are then closed with a dermal suture and dressed with steri-strips and soft dressing. Motion is started the day of surgery with 5 pound restrictions and then full activity allowed by one week.

Procedure for Endoscopic Trigger Thumb Release

A transverse incision is marked on the volar aspect of the thumb 1.5 cm distal to the proximal-proximal thumb flexion crease. This incision should be on the volar aspect of the thumb in line with the middle portion of the distal thumb flexion crease, to correspond with the flexor pollicis longus ("FPL") tendon. The incision is carried down through skin and subcutaneous tissues until the FPL tendon is visualized.

The sheath 10 is then placed over an endoscopic camera and locked into position. The sheath 10 and camera are then introduced into the incision in a distal to proximal direction. The cutting tip 34 is used to dissect over the surface of the FPL and a 1 pulley (i.e., the tight tunnel that the tendon travels through before it attaches to the bone, release of which allows easier motion and reduces the pain from trigger finger). If the Neurovascular bundle is present, it can be dissected out of the field using the shovel 30 of the sheath to protect the pulley during division. The pulley is then divided using tenotomy scissors under direct visualization. The thumb is placed through a passive flexion and extension range of motion ensuring complete release of the pulley. The instruments are then withdrawn slowly, again ensuring complete release of the pulley. The skin edges are then closed using dermal sutures and steri-strips and soft dressing applied. The patient begins immediate motion with five pound restrictions and unrestricted activity at one week.

Procedure for Endoscopic Carpal Tunnel Release and Neurolysis

A 5-10 mm transverse incision is placed 1 cm proximal to the distal volar wrist crease and ulnar to the palmaris longus tendon. This incision is carried down through the skin and subcutaneous tissue until the volar fascia is identified. The fascia is then divided using tenotomy scissors.

The sheath 10 is then placed over an endoscopic camera and locked into place. The sheath 10 and camera are then introduced into the incision from a proximal to distal direction over the volar fascia. The fascia is then divided from proximal to distal using tenotomy scissors under direct visualization. The dissection is continued distally using the cutting tip 34 of the sheath 10 to assist with soft tissue dissection over the transverse carpal ligament (extension of fascia distally). This ligament is divided using tenotomy scissors under direct visualization of the sheath 10 and camera from proximal to distal until the distal edge is completely released. During the division of the ligament the nerve will be visualized below the divided ligament ensuring complete release of pressure on the nerve.

After complete release, the sheath and camera are withdrawn slowly to obtain visualization of the median nerve and ensure no other scar tissue or other pathology exists which may cause continued symptoms of nerve compression. Any other areas of median nerve tethering or scar tissue can be released under direct visualization using the sheath and tenotomy scissors to divide the tissue. This procedure is the first endoscopic technique able to perform a neurolysis. For recurrent nerve compression and scar tissue cases, a small piece of non-adhesive barrier can he placed through the incision using a small clamp under direct visualization for placement directly on top of the median nerve to prevent further adhesions. After completion of the procedures, the sheath 10 is then withdrawn slowly ensuring complete release of the median nerve. The skin edges are closed using a dermal suture and steri-strips. Marcaine and corticosteroids and injected for post-operative pain control and the hand dressed with soft dressings. Motion is started immediately with five pound restrictions for the first week and unrestricted activity by one week.

Procedure for Endoscopic Fasciotomy for Tennis Elbow

A 1 cm longitudinal incision is placed 2 cm distal to the lateral epicondyle. This incision is carried down through the skin and subcutaneous tissues. The sheath 10 is then placed over an endoscopic camera and locked in place. The sheath 10 is then placed into the incision and the cutting tip 34 is used to dissect the soft tissue off the extensor tendon fascia. Tenotomy scissors are then used to release the fascia of the extensor carpi radialis longus, extensor carpi radialis brevus and extensor digitorum. The dissection is also carried down to the supinator, and the fascia over this muscle is also released under direct visualization of the sheath. The sheath 10 is then withdrawn slowly to ensure complete release of the fascia. The skin edges are then closed with a dermal suture and steri-strips. Soft dressing is then applied and immediate motion allowed with five pound restrictions for the first week and unrestricted activity after one week.

From the foregoing it should be apparent that endoscope sheath of the present invention provides a number of advantages over previous endoscopic tools and procedures. It provides an endoscopic surgical apparatus suitable for use in various surgical procedures that involve the dissection and/or other retraction of fibrous tissue, including an endoscopic procedure for carpal ligament release as well as other endoscopic surgical procedures. The apparatus can be used to perform such endoscopic surgical procedures with less trauma than previous endoscopic procedures. For example, during a carpel ligament release procedure, it can be placed over the carpal ligament and can provide a clear visualization of the nerve during the procedure, minimizing any trauma to the nerve and also significantly reducing any chance of injury.

Having read this disclosure, it will also be understood by those having skill in the art that modifications may be made to the invention. Therefore, the invention in its broader aspects is not limited to the specific details, representative devices, and illustrative examples shown and described. Accordingly, departures may be made from such details without departing from the spirit or scope of the general inventive concept.

What is claimed is:

1. A protective sheath for an endoscope comprising:
an elongated shaft disposed along a shaft axis and including a distal end and a proximal end and having a longitudinal bore extending from a bore proximal opening at the shaft proximal end to a bore distal opening at the shaft distal end;
wherein the longitudinal bore is sized for receiving an endoscope tube inserted axially into the bore from the shaft proximal end; and
wherein the shaft distal end includes a shovel-shaped portion comprising:
a bowl having a bowl floor and a lateral sidewall, wherein the sidewall has an inner surface and an outer surface and extends from the bowl floor to a bowl rim comprising a generally planar flange disposed opposite the bowl floor, and wherein the flange comprises a rib that is disposed generally parallel to the shaft axis and projects outwardly beyond an outermost portion of the sidewall outer surface, and
a shovel distal end that includes a generally flat surface terminating in a forward-projecting cutting edge adapted for cutting muscle, fat or other soft tissue;
wherein the generally flat surface is generally parallel to the planar flange and wherein the forward-projecting cutting edge is disposed generally perpendicular to the shaft axis for a width greater than a maximum width of the bore distal opening at the shaft distal end.

2. The sheath of claim 1 wherein the shaft proximal end includes a clip configured for attachment to an endoscopic camera.

3. The sheath of claim 1 wherein the sidewall includes a light-reflective surface.

4. The sheath of claim 1 wherein one or more surfaces of the shovel-shaped portion are adapted for retracting soft tissue during a surgical procedure.

5. The sheath of claim 1 wherein the sheath is configured for placement above a transverse carpel ligament during a carpel ligament release procedure.

6. The sheath of claim 1 wherein the forward-projecting cutting edge is disposed outside of a space bounded by:
a first plane that is generally parallel to the shaft axis and that intersects the bowl floor at an outermost point of the bowl floor; and
a second plane that is generally parallel to the first plane and that intersects a perimeter of the bore distal opening at a point that is laterally farthest from the outermost point of the bowl floor.

7. A protective sheath for an endoscope comprising:
an elongated shaft disposed along a shaft axis and including a distal end and a proximal end and having a longitudinal bore from a bore proximal opening at the shaft proximal end to a bore distal opening at the shaft distal end;
wherein the longitudinal bore is sized for receiving an endoscope tube inserted axially into the bore from the shaft proximal end;
wherein the shaft distal end includes a shovel-shaped portion comprising a bowl including a sidewall extending to a bowl rim from a bowl floor and having an inner surface and an outer surface;
wherein the bowl rim comprises a generally planar rib that projects outwardly beyond an outermost portion of the sidewall outer surface and that is disposed generally parallel to the shaft axis; and
wherein the shovel-shaped portion includes a generally flat surface that is generally parallel to the planar rib and that terminates at a forward-projecting edge disposed generally perpendicular to the planar rib for a width greater than a maximum width of the bore distal opening at the shaft distal end.

8. The sheath of claim 7 wherein the shaft proximal end includes a clip configured for attachment to an endoscopic camera.

9. The sheath of claim 7 wherein the bowl floor includes a sloped surface that extends longitudinally toward and terminates at the forward-projecting edge.

10. The sheath of claim 7 wherein the sidewall extends outwardly from the bowl floor.

11. The sheath of claim 7 wherein one or more surfaces of the shovel-shaped portion are adapted for retracting soft tissue during a surgical procedure.

12. The sheath of claim 7 wherein the forward-projecting edge is adapted for cutting muscle, fat or other soft tissue.

13. The sheath of claim 7 wherein the forward-projecting edge is disposed outside of a space bounded by:
a first plane that is generally parallel to the shaft axis and that intersects the bowl floor at an outermost point of the bowl floor; and
a second plane that is generally parallel to the first plane and that intersects a perimeter of the bore distal opening at a point that is laterally farthest from the outermost point of the bowl floor.

14. A protective sheath for an endoscope comprising:
an elongated shaft disposed along a shaft axis and including a distal end and a proximal end and having a bore extending longitudinally from a bore proximal opening at the shaft proximal end to a bore distal opening at the shaft distal end;
wherein the longitudinal bore is sized for receiving an endoscope tube inserted axially into the bore from the shaft proximal end;
wherein the shaft distal end includes a shovel-shaped portion comprising:
a bowl including a sidewall extending from a bowl floor to a bowl rim including a generally planar flange disposed opposite the bowl floor, wherein the flange comprises a rib disposed generally parallel to the shaft axis and projecting outwardly beyond an outermost portion of an outer surface of the sidewall; and
a shovel distal end comprising a generally flat surface disposed generally parallel to the shaft axis and having a forward-projecting distal edge disposed generally perpendicular to the shaft axis for a width greater than a maximum width of the bore distal opening at the shaft distal end.

15. The sheath of claim 14 wherein the shovel distal end generally flat surface has a width that is greater than the maximum width of the bore distal opening at the shaft distal end.

16. The sheath of claim 14 wherein the shovel distal end generally flat surface has a width that is greater than the maximum width of the shaft distal end.

17. The sheath of claim 14 wherein the shovel-shaped portion has a length of about 0.42 inch.

18. The sheath of claim 14 wherein the longitudinal bore within the distal shaft end has a width in a range from about 0.11 to about 0.12 inches.

19. The sheath of claim 14 wherein the shovel distal end generally flat surface has a width of about 0.27 inch.

20. The sheath of claim 14 wherein the rib extends outwardly from the sidewall about 0.03 inch.

* * * * *